US00PP28958P2

(12) United States Plant Patent
Dirr et al.

(10) Patent No.: US PP28,958 P2
(45) Date of Patent: Feb. 13, 2018

(54) ***VIBURNUM* PLANT NAMED 'PIIVIB-II'**

(50) Latin Name: *Viburnum plicatum f. plicatum*
Varietal Denomination: PIIVIB-II

(71) Applicant: Bailey Nurseries Inc., Newport, MN (US)

(72) Inventors: Michael Dirr, Bogart, GA (US); Jeff Beasley, Lavonia, GA (US); Mark Griffith, Watkinsville, GA (US); Rhonda Helvick, Madison, GA (US); Oren McBee, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 36 days.

(21) Appl. No.: 14/999,702

(22) Filed: Jun. 16, 2016

(51) Int. Cl.
*A01H 5/02* (2006.01)

(52) U.S. Cl.
USPC ..... Plt./226

(58) Field of Classification Search
None
See application file for complete search history.

*Primary Examiner* — Anne M Grunberg
(74) *Attorney, Agent, or Firm* — Penny J. Aguirre

(57) ABSTRACT

A new cultivar of *Viburnum plicata* plant named 'PIIVIB-II' that is characterized by its compact and mounding plant habit, its stems with new growth that is red in color, its floriferous blooming habit, even on young plants, its flowers that are white in color and tinted with light green and its foliage that is ovate in shape, with impressed veins, and deep green in color turning red-purple in fall and winter.

2 Drawing Sheets

Botanical classification: *Viburnum plicatum f. plicatum.*
Variety denomination: 'PIIVIB-II'.

BACKGROUND OF THE INVENTION

The present invention relates to a new and distinct cultivar of *Viburnum plicatum f. plicatum*. The new *Viburnum* will hereafter by its cultivar name, 'PIIVIB-II'. 'PIIVIB-II' represents a new cultivar of deciduous shrub grown for use as an ornamental landscape plant.

The new cultivar is the result of a controlled breeding program conducted by the Inventors in Watkinsville, Ga. The objective of the breeding program was to develop a new cultivar of *Viburnum plicatum f. plicatum* that has a compact mounded growth habit, new stems that emerge red in color and a more floriferous blooming habit with larger flowers.

The new cultivar derived from open-pollination of *Viburnum plicatum f. plicatum* 'Spellbound' (not patented) in 2009. 'PIIVIB-II' was selected in 2012 as a single unique plant from the resulting seedlings.

Asexual propagation of the new cultivar was first accomplished by one of the Inventors using semi-hardwood stem cuttings in June of 2012 in Watkinsville, Ga. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PIIVIB-II' as a unique cultivar of *Viburnum.*

1. 'PIIVIB-II' exhibits a compact and mounding plant habit.
2. 'PIIVIB-II' exhibits stems with new growth that is red in color.

3. 'PIIVIB-II' exhibits a floriferous blooming habit, even on young plants.
4. 'PIIVIB-II' exhibits flowers that are white in color and tinted with light green.
5. 'PIIVIB-II' exhibits foliage that is ovate in shape, with impressed veins, and deep green in color turning red-purple in fall and winter.

'Spellbound', the female parent of 'PIIVIB-II', differs from 'PIIVIB-II' in having an upright to columnar plant habit, in having stems with new growth that is brown in color, in having a less floriferous blooming habit with flowers that are smaller in size. 'PIIVIB-II' can be most closely compared to *Viburnum plicatum f. plicatum* cultivars 'Grandiflorum' (not patented) and 'Mary Milton' (not patented). 'Grandiflorum' is similar to 'PIIVIB-II' in having terminal cymes of white flowers, in having foliage that is dark green in color with impressed veins. 'Grandiflorum' differs from 'PIIVIB-II' in having an upright and horizontal branching habit, in having foliage that is rounded to elliptical in shape, in having flowers that are tinted pink and light green in color and in having new stem growth that is brown in color. 'Mary Milton' is similar to 'PIIVIB-II' in having a terminal flower cyme and in having foliage that is dark green in color with veins. 'Mary Milton' differs from 'PIIVIB-II' in having an upright plant habit, in having foliage with reddish bronze tinge on new growth, in having flowers that open white-green in color turning to pink and then white to pinkish white, and in having new stem growth that is brown in color.

BRIEF DESCRIPTION OF THE DRAWINGS

The accompanying colored photographs illustrate the overall appearance and distinct characteristics of the new cultivar. The plant in the photographs is about 4 years in age as grown outdoors in a trial garden in Watkinsville, Ga.

The photograph in FIG. 1 provides a side view of 'PIIVIB-II' in bloom.

Figure 1:
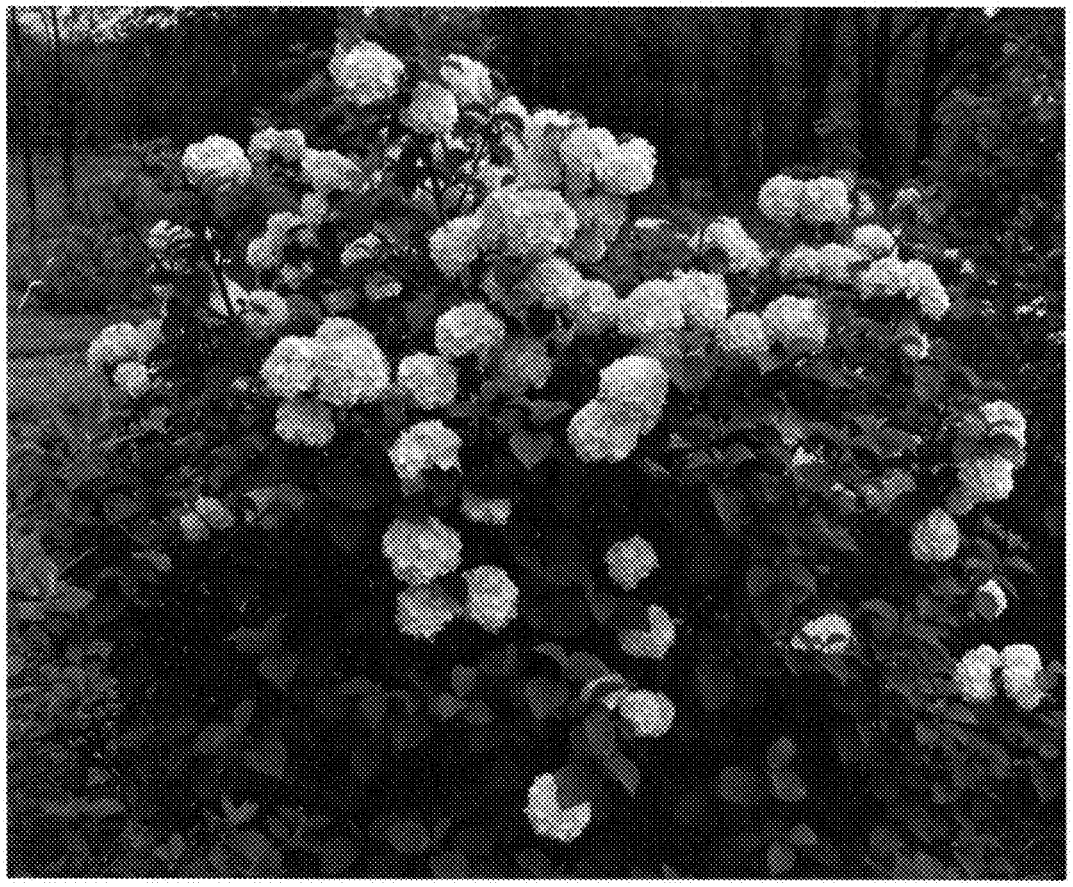
Figure 2:
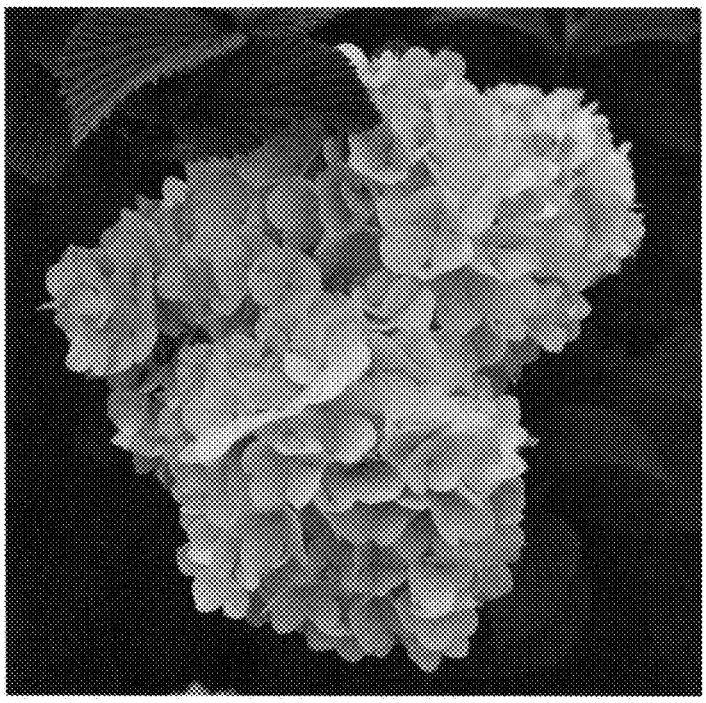

The photograph in FIG. 2 provides a close-up view of an inflorescence of 'PIIVIB-II'.

Figure 3:
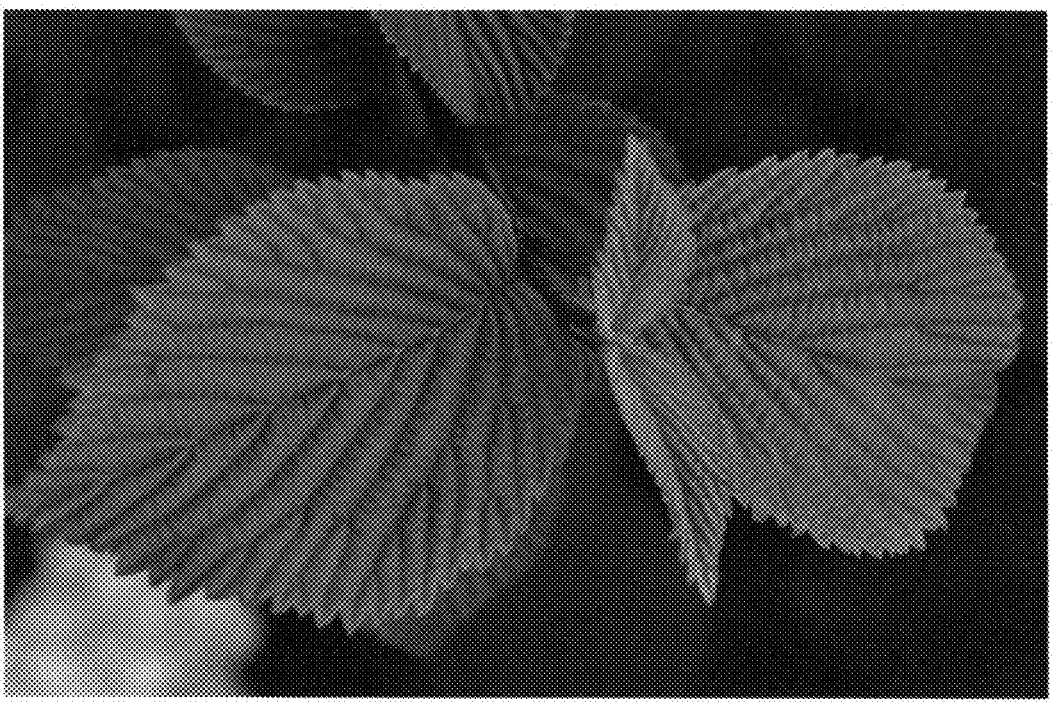

The photograph in FIG. 3 provides a close-up view of the foliage of 'PIIVIB-II' .

The colors in the photograph may differ slightly from the color values cited in the detailed botanical description, which accurately describe the colors of the new *Viburnum*.

DETAILED BOTANICAL DESCRIPTION

The following is a detailed description of 4 year-old plants of the new cultivar as grown outdoors in a trial garden in Watkinsville, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From mid April to mid May in Watkinsville, Ga.

*Plant type*.—Evergreen shrub.

*Plant habit*.—Compact, freely branched, and mounded.

*Plant size*.—An average of 1.52 m in height and spread in the landscape of as a 4 year-old plant.

*Cold hardiness*.—At least in U.S.D.A. Zones 5 to 8.

*Diseases and pests*.—No resistance to diseases or pests has been observed.

*Root description*.—Numerous, fleshy, well branched and 155A in color.

*Root habit*.—Dense, freely branching and 155A in color.

*Root development*.—Roots initiate in 5 to 6 weeks at 32° C. and produce a rooted young plant in summer about 3 months at 32° C.

*Propagation*.—Semi-hardwood stem cuttings.

*Growth rate and vigor*.—Moderate.

Branch description:

*Branch shape*.—Rounded.

*Branch color*.—Young branches; 183B, mature branches; 200A.

*Branch size*.—84 to 110 cm in length and an average of 4 mm in diameter.

*Branch surface*.—Glabrous, young stems pubescent, mature stems smooth and glabrous.

*Branch strength*.—Strong.

*Branching*.—Average of 7 lateral branches, freely branching (pinching increases branching).

*Internode size*.—Average of 2 cm.

Foliage description:

*Leaf shape*.—Ovate.

*Leaf division*.—Single.

*Leaf base*.—Rounded to cordate.

*Leaf apex*.—Acute.

*Leaf fragrance*.—None.

*Leaf venation*.—Pinnate, both surfaces 144C in color.

*Leaf margins*.—Serrate.

*Leaf arrangement*.—Opposite.

*Leaf attachment*.—Petiolate.

*Leaf surface*.—Both surfaces pubescent.

*Leaf size*.—An average of 6 cm in length and 5 cm in width.

*Leaf quantity*.—An average of 28 per lateral branch 56 cm in length.

*Leaf color*.—New growth upper surface; 143A, new growth lower surface; 143B, mature growth upper surface; 141A, mature growth lower surface 139C, fall and winter foliage upper surface; N79A, fall and winter foliage lower surface; N79C.

*Petioles*.—Average of 1.5 cm in length and 2 mm in diameter, surface pubescent and 183B in color.

Flower description:

*Inflorescence type*.—Terminal cyme.

*Lastingness of inflorescence*.—Average of 2 weeks with individual flowers lasting about 1 week.

*Inflorescence size*.—Average of 5 cm in height and 7 cm in diameter.

*Inflorescence number*.—One per lateral stem.

*Flower number*.—An average of 175 flowers per inflorescence.

*Flower fragrance*.—Faint, pleasant fragrance.

*Flower aspect*.—Upright and outward.

*Flower size*.—An average of 1 cm in diameter and 6 mm in height.

*Flower buds*.—An average of 5 cm in length and 3 mm in diameter, oval to oblong in shape, 155D in color, surface glabrous with sepal portion pubescent.

*Peduncles*.—Strong in strength, average of 2.2 cm in length and 3 mm in width, 183B in color, surface is stellate pubescent, held at various angles to stem.

*Pedicels*.—Moderate strength, an average of 1 cm in length and 5 mm in width, 183B in color, surface is stellate pubescent, held at various angles to peduncle.

*Petals*.—Average of 4 to 5 petals in a single whorl, fused at base, elliptic in shape, entire margins, obtuse to rounded apex, both surfaces smooth, 1 cm in length and width, color upper surface when opening and fully open; NN155D and tinted with 158B and 157B, color lower surface when opening and fully open; NN155D and tinted with 158B.

*Sepals*.—2, primarily obtuse in shape, serrate margins, rounded apex, both surfaces pubescent, 4 mm in length, 2 mm in width, color of inner and outer surfaces 141A.

Reproductive organs:

*Stamens*.—Average of 5, anther; is 1 mm in length, oblong in shape, 161A in color, filament; an average of 1 mm in length and 157A in color, pollen is moderate in quantity and 10B in color.

*Pistils*.—Average of 1, average of 1 cm in length, style is an average of 1 mm in length and 143D in color, stigma is round in shape and 178A in color, ovary is 144C in color.

*Seed and fruit*.—Has not been observed.

It is claimed:

1. A new and distinct cultivar of *Viburnum* plant named 'PIIVIB-II' as herein illustrated and described.

* * * * *